United States Patent [19]

Mills et al.

[11] Patent Number: 5,480,611
[45] Date of Patent: Jan. 2, 1996

[54] CARBON DIOXIDE DETECTOR

[76] Inventors: Andrew Mills, 49, Gwydr Crescent, Uplands, Swansea, West Glamorgan SA2 0AB; Qing Chang, Singleton Park, Swansea, West Glamorgan SA2 8PP, both of United Kingdom

[21] Appl. No.: 256,468
[22] PCT Filed: Jan. 11, 1993
[86] PCT No.: PCT/GB93/00049
§ 371 Date: Sep. 28, 1994
§ 102(e) Date: Sep. 28, 1994
[87] PCT Pub. No.: WO93/14399
PCT Pub. Date: Jul. 22, 1993
[51] Int. Cl.[6] .................................................. G01N 22/00
[52] U.S. Cl. ................... 422/55; 422/56; 422/57; 422/82.07; 422/82.08; 422/83; 422/85; 422/86; 422/87; 436/133; 128/719; 128/720; 128/205.23
[58] Field of Search .................. 422/55, 56, 57, 422/82.07, 82.08, 83, 85, 86, 87; 436/133; 128/719, 720, 205.23

[56] References Cited

U.S. PATENT DOCUMENTS 5,005,572 4/1991 Raenner et al. .................. 128/207.14
5,387,525 2/1995 Munkholm ........................... 436/111

FOREIGN PATENT DOCUMENTS

| 0105870 | 10/1983 | European Pat. Off. . |
| 0257916 | 8/1987 | European Pat. Off. . |
| 0283116 | 2/1988 | European Pat. Off. . |
| 0312293 | 10/1988 | European Pat. Off. . |
| 0413499 | 8/1990 | European Pat. Off. . |
| 9105252 | 4/1991 | WIPO . |

OTHER PUBLICATIONS

Munkholm, C., et al. "Polymer Modification of Fiber Optic Chemical Sensors as a Method of Enhancing Fluorescence Signal for pH Measurement.", Anal. Chem. vol. 58, 1986, 1427–1430.

Weis, L., et al. "Fiber–Optic Fluorosensor for Oxygen and Carbon Dioxide", Anal. Chem. vol. 60, 1988, 2028–2030.

*Primary Examiner*—David A. Redding

[57] ABSTRACT

The detector which provides a detectable indication of the presence of an elevated proportion of carbon dioxide compared to that in normal ambient air, comprises a substrate coated by an intimate mixture of a transparent plasticised polymer vehicle, and an indicator material which undergoes a color change on exposure to carbon dioxide. The indicator material comprises an anionic fluorimetric dye and a lipophilic organic quaternary cation.

14 Claims, 6 Drawing Sheets

CARBON DIOXIDE DETECTOR

The present invention is concerned with devices which provide a detectable indication that a volume of gas has an increased proportion of carbon dioxide compared to that present in normal ambient air. Such devices have a number of uses, one major use being to provide an indication of whether a tube has been correctly located in the airway (trachea) of a patient.

There are many clinical situations where it is necessary to place a tube in the trachea of a patient. This is done in order to supply air or a mixture of oxygen and other gases to the lungs of the patient. The correct placement of the tube in the trachea is very important. Accidents have been reported where the tube has been inadvertently placed in the oesophagus. It has been observed that the air in the trachea contains about 6% carbon dioxide, whereas the oesophagus contains air in which the concentration of carbon dioxide is normal (about 0.03%).

Several indicator devices which can detect the presence of an elevated proportion of carbon dioxide compared to that in air are known. Our prior PCT application WO91/05252 discloses a carbon dioxide monitor comprising a substrate provided with a colorimetric indicating member. The indicating member is an intimate mixture of a transparent polymer vehicle and a salt of an indicator anion and a lipophilic cation.

We have now devised a carbon dioxide detector provided with a fluorimetric sensing medium which is responsive to a carbon dioxide concentration in the proximal atmosphere. The inclusion of such fluorimetric media in a detector according to the present invention substantially enhances the sensitivity of such media in the detection of carbon dioxide.

According to the present invention therefore there is provided a carbon dioxide detector which comprises an indicating member comprising an intimate mixture of a polymer vehicle and a carbon dioxide sensing medium comprising an anionic fluorimetric dye and a lipophilic organic quaternary cation.

The response of the sensing medium to the level of carbon dioxide in the atmosphere involves the variation in the intensity of fluorescence emitted by the fluorimetric dye. The intensity of the fluorescence relies upon the fraction of the fluorimetric dye which is protonated which is in turn directly proportional to the carbon dioxide pressure. Protonation of the dye occurs via a reaction which involves both the lipophilic cation and the carbon dioxide as follows:

$$[Q^-D^-.xH_2O] - CO_2 \rightleftarrows [Q^-HCO_3^-.(x-1)H_2O.HD]$$

Flourescent        Non Flourescent where $Q^-$ is the lipophilic cation, and $D^-$ is the fluorimetric dye (excitation)=430 nm: (emission)=538 nm As can be seen from the above reaction an increase in carbon dioxide pressure will result in a decrease in fluorescence. Where a qualitative indication of carbon dioxide concentration is required the change in fluorescence can be observed visually. However, where a quantative indication of carbon dioxide concentration is required the change in fluorescence can be monitored fluorimetrically.

The above reaction illustrates how the cation/fluorimetric dye complex generates the protonated form of the dye on reaction with carbon dioxide. The fluorimetric dye, being in anionic form in the complex, readily abstracts a proton form the water molecule in the presence of carbon dioxide. Such a phase transfer mechanism is advantageous as it promotes the sensitivity of the dye in the detection of carbon dioxide.

Preferred fluorimetric dyes include 1-hydroxypyrene-3,6,8-trisulphonate, 1,3-dihydroxypyrene-6,8-disulphonate, fluorescein, umbelliferone, 4methylumbelliferone, 3-benzothiazoylbelliferone, 7-hydroxycoumarin-3-carboxylic acid, 1-naphthol-2-sulphonate, 1-naphthol-4-sulphonate, 2-naphthol-6-sulphonate, 7-hydroxyflavone, 7-hydroxyisoflavone, 3-hydroxyxanthone, 3,6-dihydroxyxanthone, 7-hydroxy-4-methylchromon, 7-hydroxylepidone, 3-hydroxyacridone, harmol methoiodide, salicylaldehyde semicarbazone and 2-hydroxycinnamic acid.

A particularly preferred dye comprises 1-hydroxypyrene-3,6,8-trisulphonate. The preference for 1-hydroxypyrene-3,6,8-trisulphonate is because of its low toxicity, a $pk_3$ value in the range of 7.3–8.1 which is advantageous for making physiological measurements. a large stoke's shift (absorption maxima of the protonated dye and non-protonated dye being 403 and 455 nm respectively, emission maximum= 512 nm, pH2–14), high photostability and high water solubility.

The detector according to the invention may, in some embodiments, be supplied in a sealed, gastight package, such as a pouch or sachet. Such a sachet may be formed from metallised polymer film, which is opaque in addition to being gas-impermeable.

When the detector according to the invention is to be used to determine whether a patient has been correctly intubated, it is preferably provided in sterilised form in such a sealed package. In this embodiment of the invention, the detector preferably consists of gamma-ray sterilisable materials.

The transparent film-forming polymer vehicle should be compatible with the cation/fluorimetric dye complex such that the latter does not exude or otherwise undergo phase separation over a prolonged period: it should in addition be hydrolytically stable in order to avoid unwanted changes in the pH in the absence of carbon dioxide. The polymer should furthermore be permeable to carbon dioxide.

The hydrolytically stable polymer may be water-soluble or organic solvent-soluble (the latter being preferred). Examples of suitable organic solvent soluble polymers include polyvinyl butyral, polyvinyl methyl ether, polymethyl methacrylate, ethyl cellulose and polystyrene.

Examples of water-soluble polymers with good resistance to hydrolysis include hydroxypropyl cellulose, methyl cellulose, carboxymethyl cellulose, polyethylene glycol, polyvinyl alcohol (100% hydrolysed) and polypropylene glycol.

According to a first aspect of the present invention, the polymer vehicle may preferably contain a plasticiser which enhances the permeability of the polymer to carbon dioxide. Preferably the plasticiser is hydrolytically stable and may be water-soluble or organic solvent-soluble (depending on the polymer vehicle).

Examples of suitable organic solvent-soluble plasticisers include alkyl triesters of phosphoric acid (including tributyl phosphate, triethyl phosphate and tris butoxyethyl phosphate), branched chain esters of carboxylic acids, especially those with secondary or tertiary alcohols (including diisopropyl phthalate and diethylhexyl sebacate), sulphamides including p-toluene sulphonamide). Examples of water-soluble plasticisers with a good resistance to hydrolysis include alcohols (including glycerine and trimethylolpropane) and ethers (including low molecular weight polyethylene glycol).

According to a second aspect of the present invention, the polymer vehicle is substantially plasticiser free. The omission of plasticiser from the polymer vehicle can be seen to optimise the fluorimetric properties of the detector when used in aqueous or high humidity conditions. This is because "fogging" (general clouding or opacity) of plasticised polymer vehicles can occur in such conditions, making qualitative measurements difficult.

Detectors which include non-plasticised polymer vehicles do not however exhibit such efficient response and recovery times as detectors which include plasticised polymer vehicles. This is illustrated by typical response and recovery times of a plasticised detector respectively being about 2.6 seconds and 31 seconds, and for a non-plasticised detector these times are respectively 5 seconds and 28 seconds.

The decision to include a plasticiser within the polymer vehicle should therefore be balanced on the required optimal properties of the detector according to the present invention. Examples of suitable quaternary cations include ammonium cations (including benzyltrimethylammonium, trioctylmethylammonium, tricaprylmethylammonium, tetrabutyl ammonium, tetrahexyl ammonium and tetraoctyl ammonium) and phosphonium cations (including tetraphenyl phosphonium, trioctyl phosphonium and hexadecyl tributyl phosphonium). A preferred quaternary cation is the tetraoctyl ammonium ion.

The salts of quaternary cations (ammonium and phosphonium) become insoluble in water when the cation is above a certain molecular weight (approximately C24 in the case of symmetrical aliphatic quaternary ammoniums). This phenomenon may be exploited to confer enhanced water resistance on non-aqueous sensor films by rendering the dye and buffer components immune to dissolution and "wash out" by liquid water.

Preferably the indicating member of the detector is provided, typically in the form of a film of thickness of about 20 microns, on a substrate. The substrate should be such that it is free of mobile components capable of migrating into the indicating film: equally it should resist migration of components from the latter film. Furthermore, the substrate should be chemically inert relative to the film.

Suitable inorganic materials for use as the substrate include glasses, ceramics, and crystalline materials: suitable organic materials include paper, polyolefins (such as polypropylene or polyethylene) and fluorocarbons (such as PTFE). When polymers are used, they should be free of reactive or migratory plasticisers, lubricants, antioxidants or the like. The substrate may be in the form of a simple tube or plate: in one preferred embodiment the substrate is in the form of a connector or junction piece for a catheter. In another embodiment of the invention, the substrate may be in the form of a tube which is open at both ends: this may be used to monitor the carbon dioxide content of expired breath in a method in which the patient breaths through the tube and the fluorescence change in the indicator film monitored. This method may be used for determination of the end-tidal carbon dioxide (that is, the carbon dioxide present in the final expiration of a deep breath from the lungs).

The carbon dioxide sensor according to the invention may be used for long term continuous monitoring of carbon dioxide concentration if acidifying and oxidising gases are removed from the air prior to contact with the film. This may be achieved using a "guard" or "scrubbing" device incorporating (i) the salt of an involatile acid with a pKa intermediate between carbonic acid and the polluting volatile acid (e.g. sulphurous acid) and (ii) an antioxidant or antiozonant. The sensor typically has a shelf life of over six months, this shelf life can however be depeited by prolonged exposure of the detector polymer vehicle to a dry environment or substantial heating.

There is further provided by the present invention a method of preparing a carbon dioxide detector as hereinbefore described, which method comprises mixing an anionic fluorimetric dye, a lipophilic quaternary cation and a polymer to produce a carbon dioxide indicating member, and substantially curing said indicating member.

Typically the indicating member is cast as a film on a substrate, and curing of the film results in a decrease in film thickness generally from about 100 microns (as applied) to about 20 microns (when cured).

Typical reagents used in the method are substantially as hereinbefore described with reference to the detector.

There is further provided by the present invention a carbon dioxide detector obtained by a method as described above.

The present invention will now be further illustrated by the following example, in which is described a method of preparation of a carbon dioxide detector according to the present invention, and spectrophotometric analysis of the polymer film of the detector.

BRIEF DESCRIPTION OF THE DRAWINGS

Reference will now be made to the accompanying drawings, in which.

Figure 1:
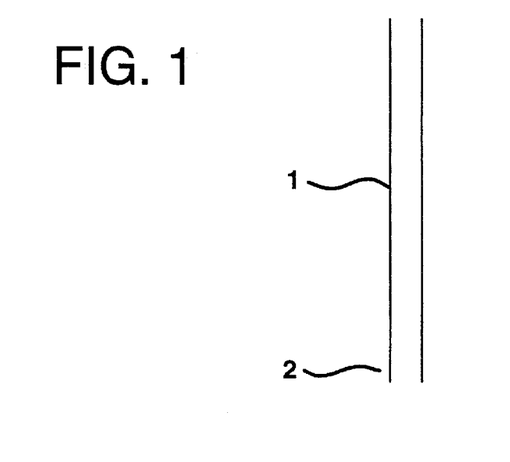
FIG. 1 is a side elevation showing one form of a detector according to the invention.

Referring to FIG. 1, there is shown a device comprising a relatively gas-impermeable tube 1, the internal surface thereof being provided with a coating of fluorimetric sensing material.

Figure 2:
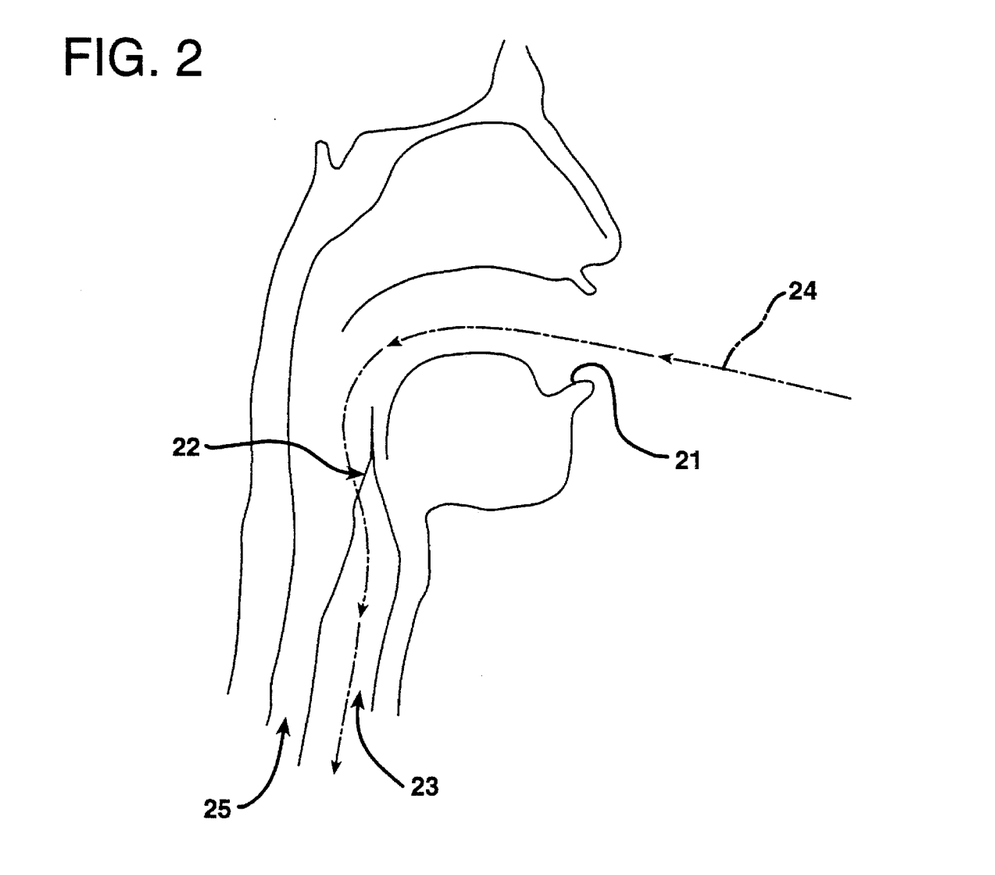
FIG. 2 is a simplified anatomical diagram showing how correct intubation of the trachea is effected.

Referring to FIG. 2, a portion of a head and neck is shown; passing along the mouth 21, through the epiglottis 22 to the trachea 23 is a dotted line 24 showing the path of correct intubation. If the tracheal tube failed to pass through the epiglottis, it would pass down the oesophagus 25 in error.

If a device such as that illustrated in FIG. 1 were to be passed along the tracheal tube, when the leading edge thereof reaches the tracheal zone, the device would respond to the higher carbon dioxide content by undergoing a change of intensity of fluorescence emitted by the indicator layer. On the contrary, if the leading end of the device were to be located erroneously in the oesophagus, there would be no resulting change in fluorescence intensity. This therefore provides a simple and effective test for whether or not a tracheal tube has been correctly inserted in the trachea.

The present invention has been described primarily with reference to a device for use in determining whether a patient has been correctly intubated; other uses of a monitor according to the invention are envisaged, such as for use as a personnel monitor for use in potentially hazardous environments, such as ships' holds, tanks or the like.

EXAMPLE

A film solution was prepared by mixing together $2.07 \times 10^{-3}$ mol dm$^{-3}$ 1-hydroxypyrene-3,6,8-trisulphonate (HPTS) in methanol (2 cm$^3$), 0.2 mol dm$^{-3}$ tetraoctylammonium hydroxide in methanol, 10 g of a solution comprising 10 g of ethyl cellulose dissolved in 20 cm$^3$ ethanol and 80 cm$^3$ toluene, and 2 cm$^3$ of tris-n-butyl phosphate.

A film was cast from the film solution onto the surface of a gas impermeable tube as illustrated in FIG. 1. As cast, the film was approximately a 100 micron thick layer (using a brass template) and was reduced to a thickness of about 20 microns when dried. Thicker films, of thickness of about 40 microns, could of course be prepared.

Spectrophotometric and steady-state fluorimetric analysis of the film were respectively carried out using a Perkin Elmer Lambda 9 UV/VIS/NIR spectrophotometer and a Perkin Elmer LS-5 Fluorimeter/Phosphorimeter.

In measurement of the response of the film, as a function of time, to rapid variations in the level of the ambient $CO_2$, an optical system with a resolution of ca. 12 ms. was used. This system comprises a 100 W quartz-iodide lamp coupled with 430 nm interference filter (half band width$\pm$40 nm) which was used to excite the dye in the thin film (at right-angles to the excitation beam). The emission from the edge of the film passed through a high resolution monochromator (Applied Photophysics, U.K.) set at 517 nm and the intensity of the emission at the wavelength was measured using a photomultiplier. In the measurement of the response and recovery times a rapid-switching gas administration system was used.

In order to provide a spectrophotometric comparison of the absorption spectra of the protonated and non-protonated forms of the film, the film was exposed to: (i) an atmosphere of 100% $N_2$, and (ii) an atmosphere of 100% $CO_2$. Exposure of the film to a high level of $CO_2$ is able to completely convert the deprotonated form of the dye into its protonated form (wavelength of maximum absorption=394 nm). It can be readily demonstrated that this process is reversible and can be repeated many times over a period of a day with little or no evidence of degradation in film performance.

Protonation of the film, and measurement of its absorption spectrum, were carried out.

Figure 3:
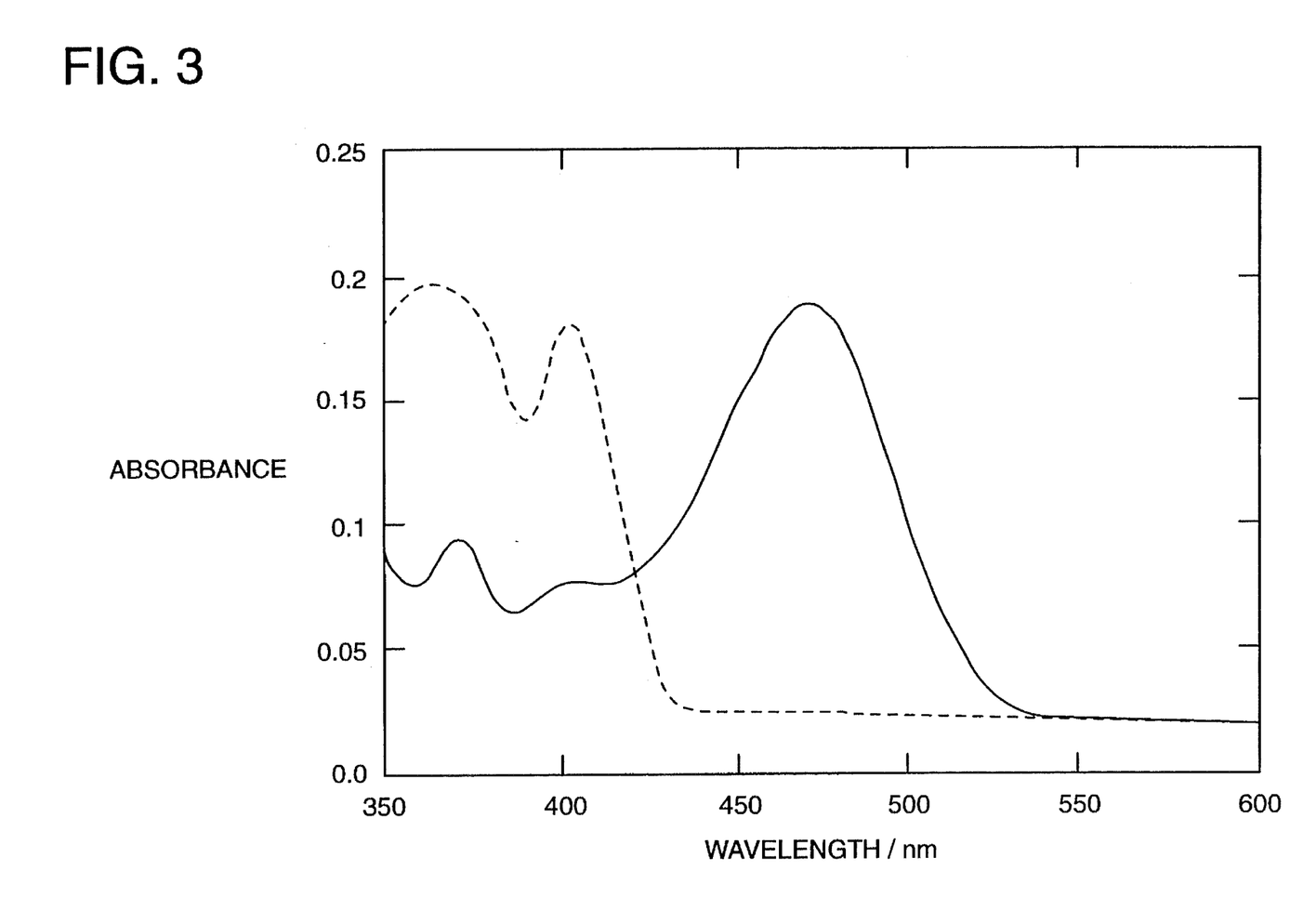
FIG. 3 shows the absorption spectra of a sensor according to the present invention when exposed (i) to $CO_2$ (maximum absorption 394 nm as shown in broken line) and (ii) to nitrogen (maximum absorption 467 nm)

FIG. 3 shows the absorption spectra of the film when exposed to (i) $CO_2$ (maximum absorption 394 nm) and (ii) to nitrogen (maximum absorption 467 nm) as described above.

From the inspection of the absorption spectra in FIG. 3 an excitation wavelength of 430 nm was employed to study the effect of $CO_2$ upon the intensity of film fluorescence. This is because the wavelength of 430 nm excites the deprotonated form of the dye exclusively and therefore avoids the complicating factor of exciting the protonated form of the dye.

The fluorescence due to the excited form of deprotonated HPTS present in the film has a maximum at 517 nm (slightly red shifted compared to 512 nm for HPTS in aqueous solution). 517 nm was then chosen as the emission wavelength at which the fluorescence intensity of the film was measured as a function of % $CO_2$.

Figure 4A:
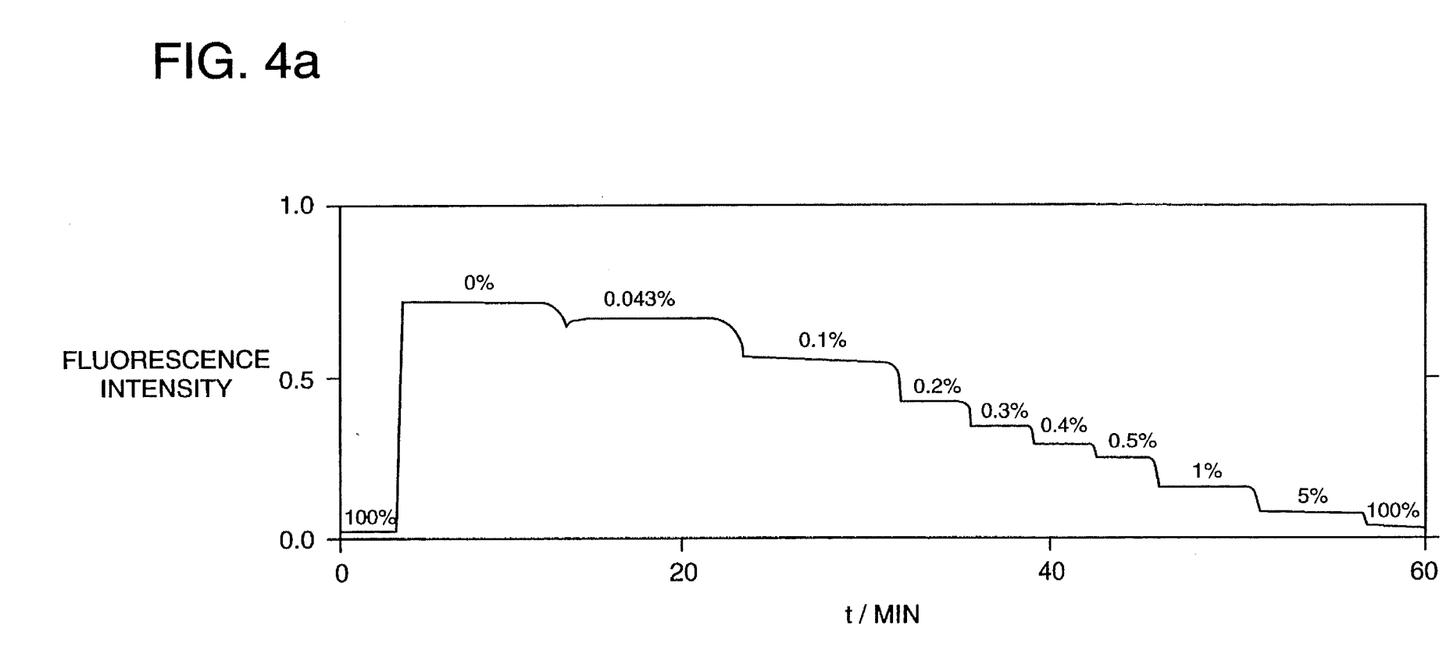
FIG. 4a shows the variation of fluorescence intensity of the film with % $CO_2$ and time (excitation wavelength 430 nm, emission wavelength 517 nm), and FIG. 4b the subsequent plot of the data in the form of fluorescence intensity versus % $CO_2$.
Figure 4B:
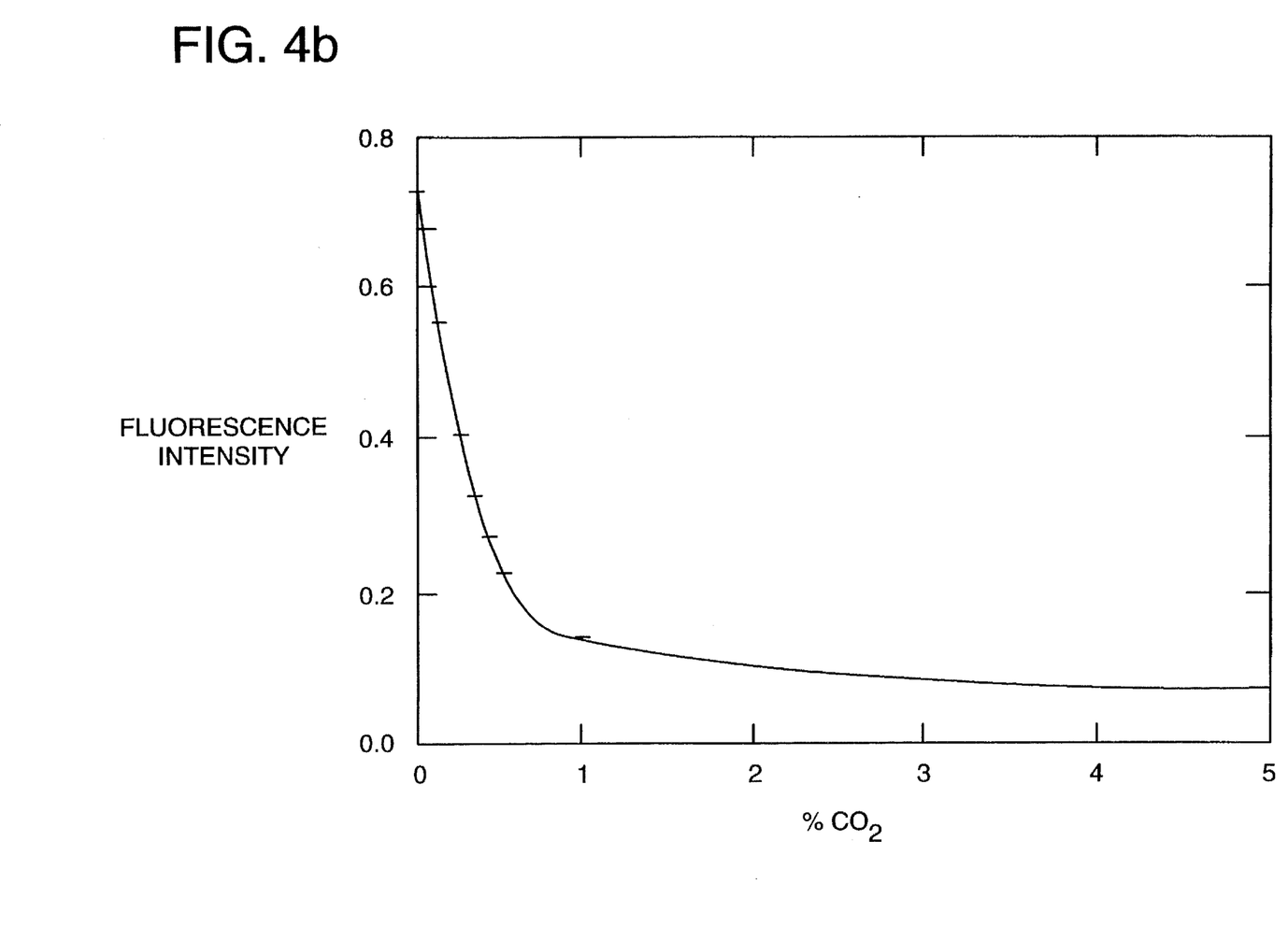

FIG. 4a shows the variation of fluorescence intensity of the film with % $CO_2$ and time (excitation wavelength 430 nm, emission wavelength 517 nm), and FIG. 4b the subsequent plot of the data in the form of fluorescence intensity versus % $CO_2$.

The plot of fluorescence intensity versus % $CO_2$ illustrated in FIG. 4b is similar in shape to the profile expected for a direct sensor, i.e. one in which there is a 1:1 equilibrium reaction between the analyte and the "immobilised" reagent. This situation would arise if the overall interaction between $\{Q^+D^-.xH_2O\}$ and $CO_2$ was as follows:

$$\{Q^-D^-.xH_2O\} + CO_2(g) \underset{\longleftarrow}{\overset{K}{\longrightarrow}} \{Q^-HCO_3^-.(X-1)H_2O.HD\}$$

It follows that the relationship between the % $CO_2$ present and the concentrations of $\{Q^+D^-.xH_2O\}$ and $\{Q^+HCO_3^-(x-1)H_2O.HD\}$ will be given by the following expression:

$$\% \ CO_{2.xK} = [\{Q^+HCO_3^-(x-1)H_2O.HD\}]/[\{Q^+D^-.xH_2O\}]$$

The film was subsequently exposed to a gas stream alternating in $CO_2$:$N_2$ composition from 5%:95% to 0%:100% every 20 s: this was achieved using two pressure actuator, solenoid activated valves. From the resulting measured variation in the fluorescence intensity of the film the 0 to 90% response (0% $CO_2$ to 5% $CO_2$) and recovery (5% $CO_2$ to 0% $CO_2$) times for the film were respectively found to be 4.3 and 7.1 s.

In another set of experiments, the % $CO_2$ in the gas phase was varied randomly with time and the response of the film monitored, so as to estimate the potential of a detector according to the present invention for use as a continuous $CO_2$ sensor. At the same time the % $CO_2$ in the gas phase was also monitored using a commercial capnostat, i.e. an infra-red $CO_2$ detector ("End Tidal $CO_2$ monitor", model 1260, Novametric Medical Systems Inc. U.S.A.).

Figure 5A:
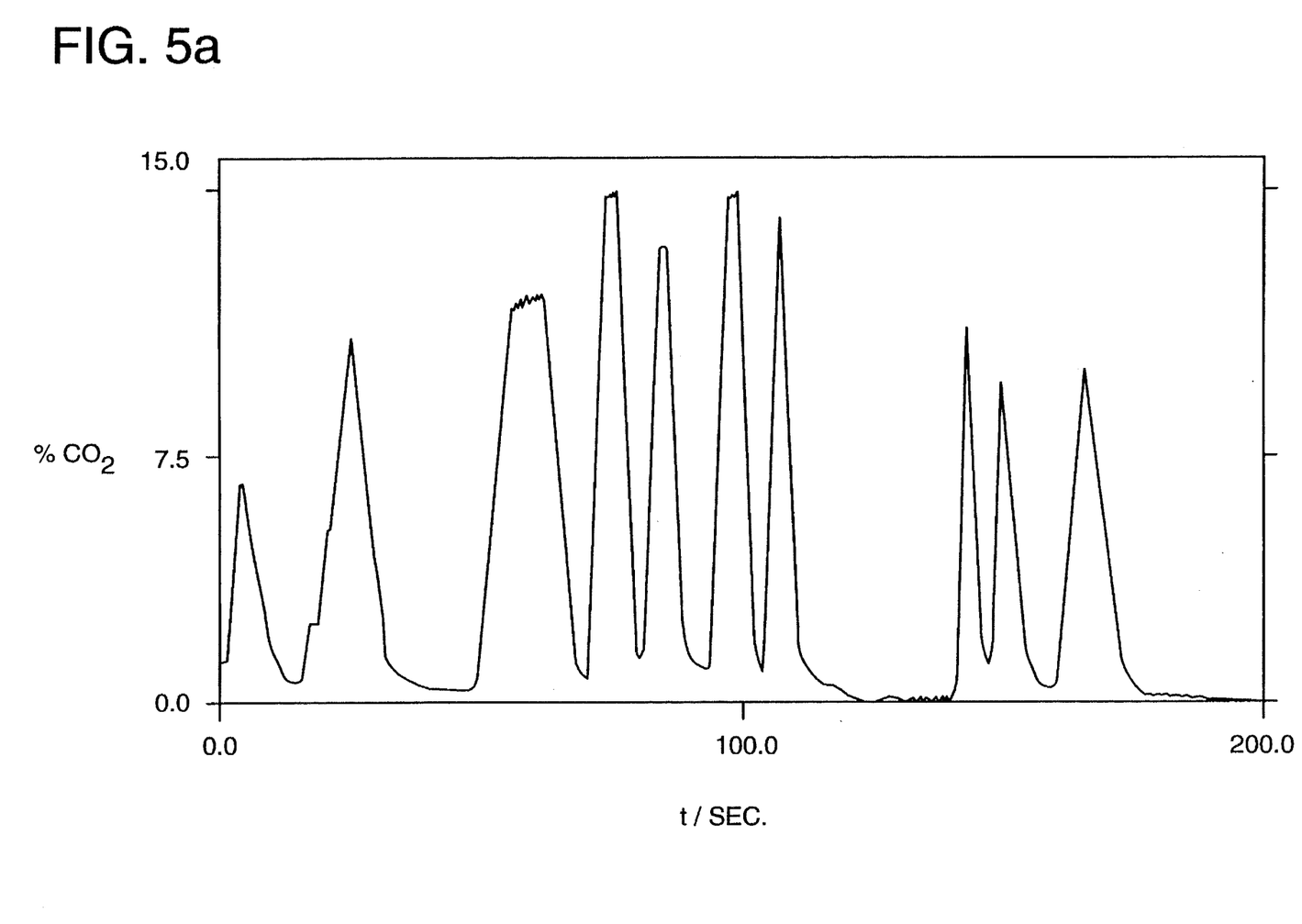
FIG. 5a shows the output of a commercially available capnostat when exposed to an atmosphere of varying $CO_2$ concentration, and FIG. 5b the output from a sensor according to the present invention when exposed to the same atmosphere.
Figure 5B:
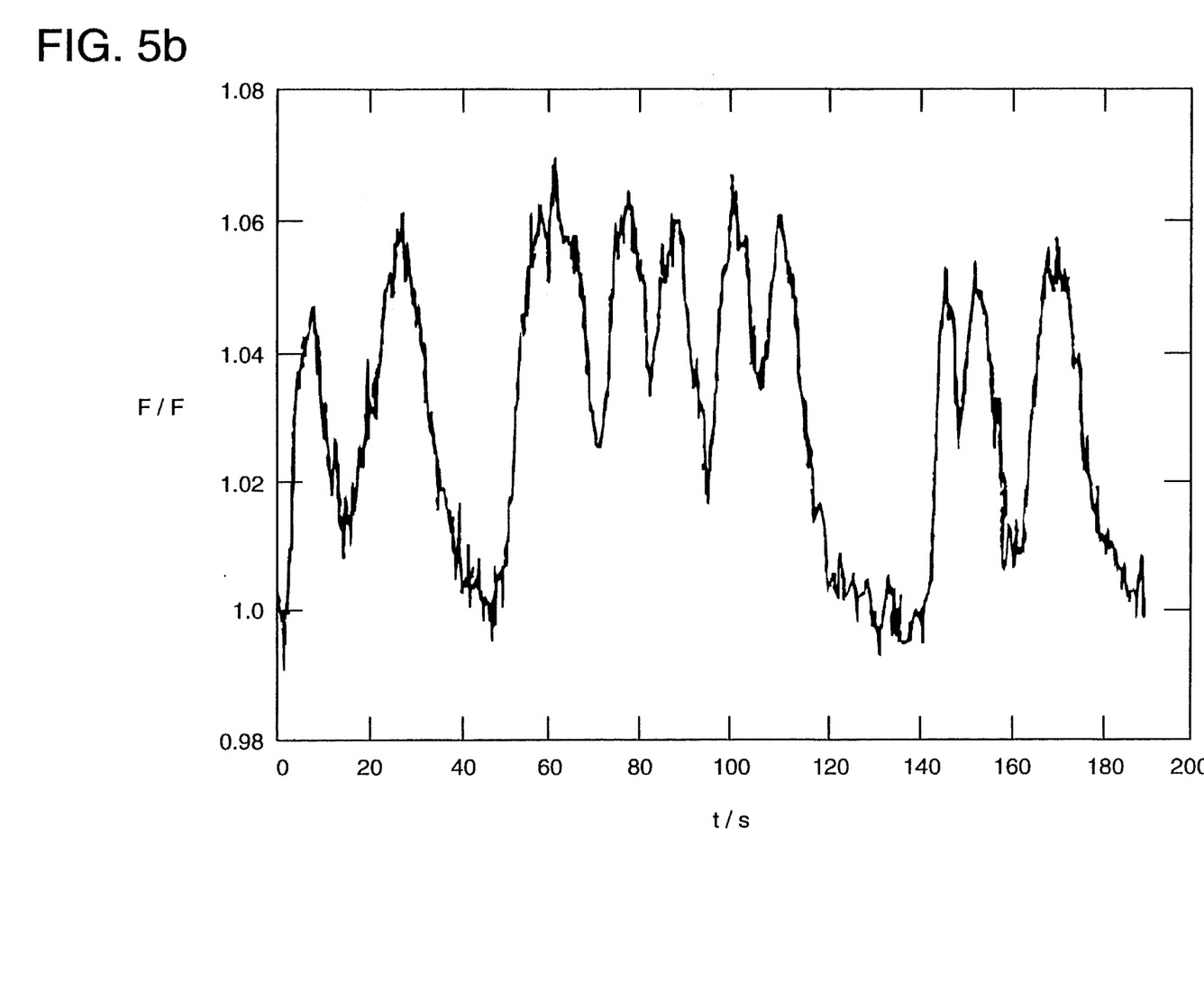

The output from the capnostat and the film are illustrated in FIGS. 5(a) and 5(b), respectively, and the reasonable degree of matching shows the suitability of a detector according to the present invention for continuous $CO_2$ sensing.

We claim:

1. A carbon dioxide detector which comprises an indicating member comprising an intimate mixture of a polymer vehicle and a carbon dioxide sensing medium comprising an anionic fluorimetric dye and a lipophilic organic quaternary cation.

2. A detector according to claim 1, wherein said fluorimetric dye comprises any of 1,3-dihydroxypyrene-6,8-disulphonate,fluorescein,umbelliferone,4-methylumbelliferone,3-benzothiazoylbelliferone, 7-hydroxycoumarin-3-carboxylic acid, 1-naphthol-2-sulphonate, 1-naphthol-4-sulphonate, 2-naphthol-6-sulphonate, 7-hydroxyflavone, 7-hydroxyisoflavone, 3-hydroxyxanthone, 3,6-dihydroxyxanthone, 7-hydroxy-4-methylchromon, 7-hydroxylepidone, 3-hydroxyxacridone, harmol methoiodide, salicylaldehyde semicarbazone and 2-hydroxycinnamic acid.

3. A detector according to claim 1, wherein said fluorimetric dye comprises 1-hydroxy-3,6,8-trisulphonate.

4. A detector according to claim 1, wherein said indicating member is in the form of a film provided on a substrate.

5. A detector according to claim 4, wherein said film has a thickness of about 20 microns.

6. A detector according to claim 1, which consists of gamma-ray sterilisable materials.

7. A detector according to claim 1, wherein said polymer vehicle comprises any of polyvinyl butyral, polyvinyl methyl ether, polymethyl methacrylate, ethyl cellulose and polystyrene.

8. A detector according to claim 1, wherein said polymer vehicle comprises any of hydroxypropyl cellulose, methyl cellulose, carboxymethyl cellulose, polyethylene glycol, polyvinyl alcohol and polypropylene glycol.

9. A detector according to claim 1, wherein said polymer vehicle contains a plasticiser.

10. A detector according to claim 9, wherein said plasticiser comprises any of tributyl phosphate, triethyl phosphate, tris butoxyethyl phosphate, diisopropyl phthalate, diethylhexyl sebacate, and p-toluene sulphonamide.

11. A detector according to claim 9, wherein said plasticiser comprises any of glycerine, trimethylolpropane and low molecular weight polyethylene glycol.

12. A detector according to claim 1, wherein said polymer vehicle is substantially plasticiser free.

13. A detector according to claim 1, wherein said quaternary cation comprises any of benzyltrimethyl ammonium, trioctylmethyl ammonium, tricaprylmethyl ammonium, tetrabutyl ammonium, tetrahexyl ammonium, tetraphenyl phosphonium, trioctyl phosphonium and hexadecyl tributyl phosphonium.

14. A detector according to claim 1, wherein said cation comprises tetraoctyl ammonium.

* * * * *